(12) United States Patent
Chiffon et al.

(10) Patent No.: US 7,429,353 B2
(45) Date of Patent: Sep. 30, 2008

(54) METHOD AND APPARATUS FOR INJECTING A METERED QUANTITY OF A LIQUID INTO A CHAMBER

(75) Inventors: Mark E. Chiffon, Erie, PA (US); Peter J. Buczynski, Girard, PA (US); Kenneth J. Klobusnik, Lake City, PA (US); Kimberly R. Goray, Erie, PA (US)

(73) Assignee: American Sterilizer Company, Mentor, OH (US)

( * ) Notice: Subject to any disclaimer, the term of this patent is extended or adjusted under 35 U.S.C. 154(b) by 510 days.

(21) Appl. No.: 11/186,536

(22) Filed: Jul. 21, 2005

(65) Prior Publication Data

US 2007/0020141 A1 Jan. 25, 2007

(51) Int. Cl.
*A61L 2/20* (2006.01)
*B67D 5/30* (2006.01)

(52) U.S. Cl. .................. 422/33; 422/292; 222/14; 222/309; 222/340

(58) Field of Classification Search .......... None
See application file for complete search history.

(56) References Cited

U.S. PATENT DOCUMENTS

| | | | |
|---|---|---|---|
| 4,169,123 A | 9/1979 | Moore et al. ............ 422/29 |
| 4,169,124 A | 9/1979 | Forstrom et al. ............ 422/33 |
| 4,230,663 A | 10/1980 | Forstrom et al. ............ 422/33 |
| 4,512,951 A | 4/1985 | Koubek ................ 422/33 |
| 4,642,165 A | 2/1987 | Bier ................. 203/12 |
| 4,744,951 A | 5/1988 | Cummings et al. ........... 422/28 |
| 4,909,999 A | 3/1990 | Cummings et al. ......... 422/298 |
| 5,122,344 A | 6/1992 | Schmoegner ............ 422/111 |
| 5,413,758 A | 5/1995 | Caputo et al. ............ 422/22 |
| 5,445,792 A | 8/1995 | Rickloff et al. ............ 422/28 |
| 5,492,672 A | 2/1996 | Childers et al. ............ 422/28 |
| 5,527,507 A | 6/1996 | Childers et al. ............ 422/28 |
| 5,759,486 A | 6/1998 | Peterson ................ 422/21 |
| 5,788,925 A | 8/1998 | Pai et al. ............... 422/3 |
| 6,656,426 B1 | 12/2003 | Wang et al. ............ 422/27 |
| 6,699,434 B1 | 3/2004 | Lukasik et al. ............ 422/33 |
| 6,752,959 B2 | 6/2004 | Smith et al. ............ 422/28 |

*Primary Examiner*—Elizabeth L McKane
(74) *Attorney, Agent, or Firm*—Kusner & Jaffe; Michael A. Centanni

(57) ABSTRACT

A method and apparatus for metering a predetermined quantity of liquid decontaminant into a vaporization system. A single vacuum source is used to fill an injector with the predetermined quantity of liquid decontaminant and to also establish a vacuum in a chamber. The chamber is injected with the liquid decontaminant filling the injector. The liquid decontaminant is vaporized in the chamber to produce a vaporized decontaminant.

17 Claims, 3 Drawing Sheets

US 7,429,353 B2

METHOD AND APPARATUS FOR INJECTING A METERED QUANTITY OF A LIQUID INTO A CHAMBER

FIELD OF THE INVENTION

The present invention relates generally to a method and apparatus for metering a liquid, and more particularly to a method and apparatus for metering a liquid decontaminant into a vaporization system, where the vaporized decontaminant produced by the vaporization system is typically used in a decontamination process.

BACKGROUND OF THE INVENTION

Generally, in a vapor phase decontamination process (e.g., deep vacuum sterilization), a liquid decontaminant is metered from a reservoir or other container into a vaporizer or decontamination chamber in which vaporization occurs. In this regard, a deep vacuum is drawn inside the chamber, and a metered amount of liquid decontaminant is then drawn into the chamber, where it vaporizes in the deep vacuum. To ensure effective and efficient decontamination, the liquid decontaminant should be metered in accurately and reproducibly measured amounts.

Prior art approaches for metering a liquid decontaminant have been complex and costly due to the need for such components as an electronic balance, multiple pumps or external pressure sources for drawing vacuums at different locations within a system. Accordingly, there is a need for a simpler and less costly approach for delivering metered amounts of a liquid decontaminant to a vaporization chamber. The present invention addresses these and other deficiencies of the prior art.

SUMMARY OF THE INVENTION

In accordance with the present invention, there is provided a system for metering a predetermined quantity of a liquid decontaminant into a chamber, the system comprising: a vacuum source; a source of the liquid decontaminant; a reservoir for storing the liquid decontaminant; and an injection means for injecting a predetermined quantity of liquid decontaminant into the chamber, wherein the reservoir is fluidly connectable with the source of the liquid decontaminant, the injection means, and the vacuum source; the injection means is fluidly connectable with the chamber and the vacuum source; and the chamber is fluidly connectable with the vacuum source.

In accordance with another aspect of the present invention, there is provided a method for metering a predetermined quantity of a liquid decontaminant into a chamber, the method comprising: transferring a liquid decontaminant from a source of liquid decontaminant to a reservoir by putting the reservoir in fluid communication with the source of liquid decontaminant and with a vacuum source; transferring the liquid decontaminant from the reservoir to an injection means by putting the reservoir in fluid communication with the injection means, and putting the injection means in fluid communication with the vacuum source; and metering liquid decontaminant from the injection means to the chamber by putting injection means in fluid communication with the chamber having a vacuum created therein.

An advantage of the present invention is the provision of a method and apparatus for metering a liquid decontaminant that efficiently uses a single vacuum pump to draw fluids throughout a system.

Another advantage of the present invention is the provision of a method and apparatus for metering a liquid decontaminant that is less costly than prior art approaches.

Still another advantage of the present invention is the provision of a method and apparatus for metering a liquid decontaminant that is less complex than prior art approaches.

Still another advantage of the present invention is the provision of a method and apparatus for metering a liquid decontaminant that provides improved accuracy and consistency by removing air bubbles from the system prior to filling an injector with a metered quantity of liquid decontaminant.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 1 is a schematic diagram of a system for metering a liquid decontaminant into a vaporization system, according to a preferred embodiment of the present invention, wherein FIG. 1 illustrates a reservoir fill operation;

DETAILED DESCRIPTION OF A PREFERRED EMBODIMENT

As used herein, the term "decontaminant" includes, but is not limited to a chemical agent used as a sterilant, disinfectant, and the like. The term "decontamination" includes, but is not limited to, sterilization, disinfection and sanitation.

Figure 1:
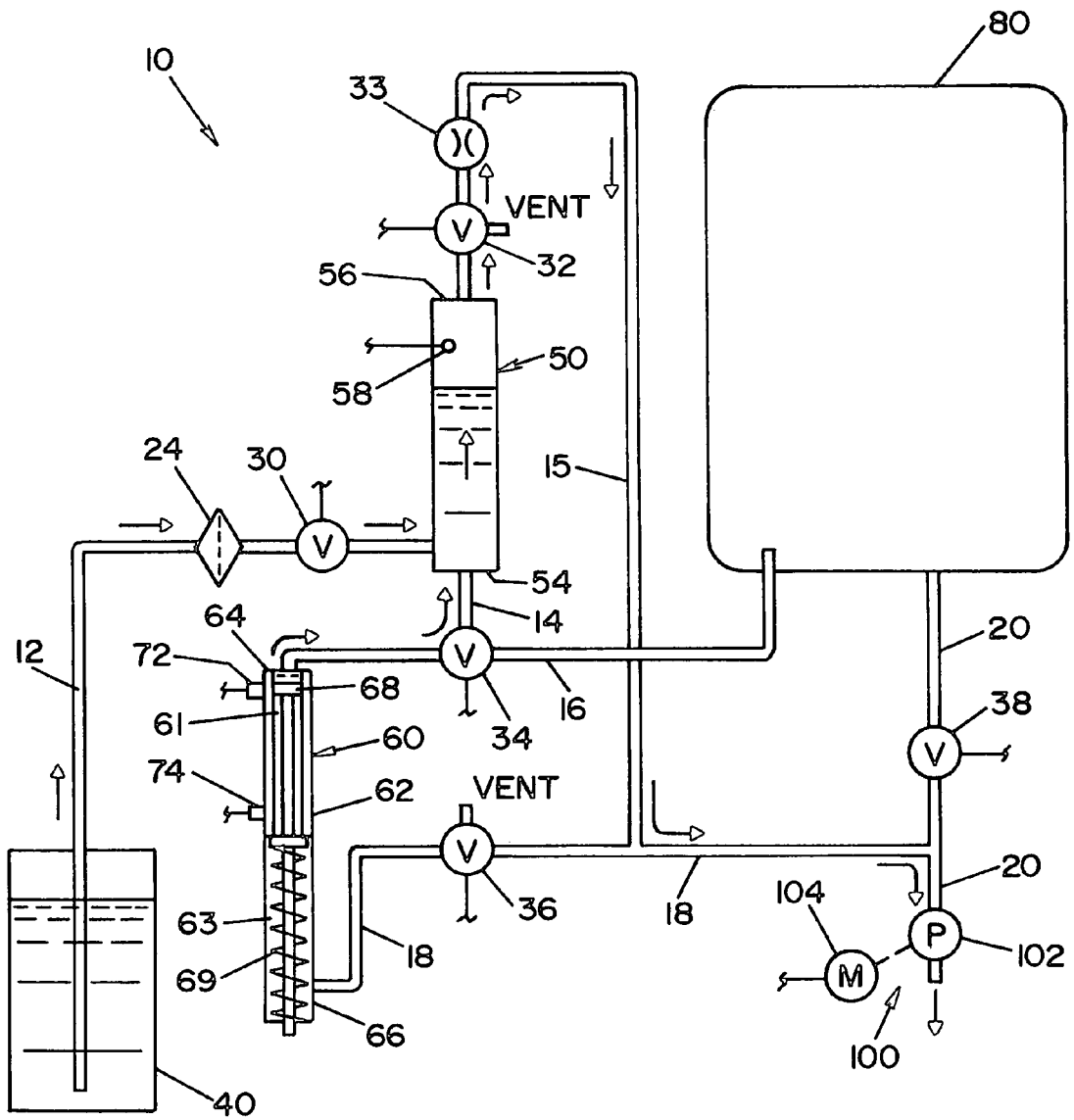

Referring now to the drawings wherein the showings are for the purposes of illustrating a preferred embodiment of the invention only and not for the purposes of limiting same, FIG. 1 shows a system 10 for metering a liquid decontaminant into a vaporization system. In the illustrated embodiment, vaporization system is a chamber 80. It should be appreciated that chamber 80 may be a decontamination chamber, a vaporization chamber, or the like.

System 10 is generally comprised of a plurality of fluid conduits (described below) defining a plurality of fluid pathways, a decontaminant source 40, a reservoir 50, an injector 60, a vacuum source 100, and a plurality of valves (described below).

Decontaminant source 40 provides a bulk supply of a liquid decontaminant (e.g., an aqueous solution of hydrogen peroxide). By way of example, and not limitation, decontaminant source 40 may take the form of a vessel, a tank, a bottle, or other container suitable for storing liquid.

Reservoir 50 has a first end 54 and a second end 56. Reservoir 50 may take the form of an enclosed container, such as a vessel, a tank or bottle. In a preferred embodiment, reservoir 50 is dimensioned to store a volume of liquid decontaminant sufficient for at least one complete decontamination cycle. A level sensor 58 is associated with reservoir 50 to sense the fluid level therein. Level sensor 58 may be located inside or outside reservoir 50.

In the illustrated embodiment, injector 60 is generally comprised of a cylinder 62, and a piston 68. Injector 60 has a first port at a first end 64 and a second port at a second end 66. In the illustrated embodiment, cylinder 62 has a head section 61 for collecting liquid decontaminant and a spring section 63 that receives a spring 69. Spring 69 acts as a bias means to bias piston 68 toward the first port at first end 64. Injector 60 also includes a first limit switch 72 and a second limit switch 74. Limit switches 72 and 74 provide an indication of the position of piston 68 within cylinder 62. In this regard, first limit switch 72 is activated when piston 68 is located at a first position inside cylinder 62. Second limit switch 74 is activated when piston 68 is located at a second position inside cylinder 62. When piston 68 is located at the second position inside cylinder 62, head section 61 contains a predetermined volume of liquid decontaminant, as will be described in further detail below. It should be appreciated that injector 60 may have alternative forms, including, but not limited to, a syringe, a bladder, a chamber or a vessel. In a preferred embodiment, injector 60 is dimensioned to store a volume of liquid decontaminant for a single pulse of the decontamination cycle.

According to an illustrated embodiment of the present invention, vacuum source 100 is comprised of a pump 102 driven by a motor 104. Pump 102 is used to generate a vacuum, as will be described in detail below. In a preferred embodiment, pump 102 has the capacity to generate a vacuum in the range of about 0.0001 Torr to about 760 Torr.

A control unit (not shown) is provided to control operation of vacuum source 100, actuate valves, and receive sensor data signals from level sensor 58 and switches 72 and 74. By way of example, and not limitation, the control unit may include a microprocessor or microcontroller.

First end 54 of reservoir 50 is fluidly connectable with decontaminant supply 40 and first end 64 of injector 60. Second end 56 of reservoir 50 is fluidly connectable with vacuum source 100. First end 64 of injector 60 is fluidly connectable with first end 54 of reservoir 50 and chamber 80. Second end 66 of injector 60 is fluidly connectable with vacuum source 100. Chamber 80 is fluidly connectable with first end 64 of injector 60 and vacuum source 100.

The fluid conduits connecting with decontaminant source 40, reservoir 50, injector 60, chamber 80 and vacuum source 100 will now be described with reference to the illustrated embodiment. The arrangement of fluid conduits of the illustrated embodiment is exemplary, and is not intended to limit the scope of the present invention. It should be appreciated that the present invention can be practiced using alternative arrangements of the fluid conduits.

A first conduit 12 is in fluid communication with decontaminant source 40 and first end 54 of reservoir 50. A first valve 30 is disposed in first conduit 12 between decontaminant source 40 and reservoir 50 to regulate fluid flow through first conduit 12. In the illustrated embodiment, a filter 24 is also provided in first conduit 12 to filter the liquid decontaminant before it is received by reservoir 50.

A second conduit 14 is in fluid communication with first end 54 of reservoir 50 and a fourth conduit 16, described below.

A third conduit 15 is in fluid communication with second end 56 of reservoir 50 and a fifth conduit 18, described below. A second valve 32 is disposed in third conduit 15 between reservoir 50 and fifth conduit 18 to regulate fluid flow therethrough. Valve 32 is a three-way valve having first and second ports connected with third conduit 15, and a third port connected with a vent to atmospheric pressure. In the illustrated embodiment valve 32 has only two positions. In a first position, valve 32 puts second end of reservoir 56 in fluid communication with a vent to atmospheric pressure. In a second position, valve 32 puts second end of reservoir 50 in fluid communication with vacuum source 100. In the illustrated embodiment, a restrictor valve 33 is disposed in third conduit 15 between second valve 32 and fifth conduit 18. Restrictor valve 33 provides a controlled fluid flow rate through conduit 15.

Fourth conduit 16 is in fluid communication with first end 64 of injector 60, second conduit 14, and chamber 80. A third valve 34 is disposed in fourth conduit 16. Valve 34 is a three-way valve having first and second ports connected with fourth conduit 16 and a third port connected with second conduit 14. Accordingly, fluid flow through conduits 14 and 16 is regulated by valve 34. In the illustrated embodiment, valve 34 has only two positions. In a first position (i.e., default position), valve 34 puts first end 54 of reservoir 50 in fluid communication with first end 64 of injector 60. In a second position, valve 34 puts chamber 80 in fluid communication with first end 64 of injector 60.

Fifth conduit 18 is in fluid communication with second end 66 of injector 60, third conduit 15, and a sixth conduit 20, described below. A fourth valve 36 is disposed in fifth conduit 18. Valve 36 is a three-way valve having first and second ports connected with fifth conduit 18, and a third port connected with a vent to atmospheric pressure. In the illustrated embodiment, valve 36 has only two positions. In a first position (i.e., default position), valve 36 puts second end 66 of injector 60 in fluid communication with a vent to atmospheric pressure. In a second position, valve 36 puts second end 66 of injector 60 in fluid communication with vacuum source 100. Third conduit 15 is in fluid communication with fifth conduit 18 between valve 36 and sixth conduit 20.

Sixth conduit 20 is in fluid communication with chamber 80, fifth conduit 18, and vacuum source 100. A fifth valve 38 is disposed in sixth conduit 20 to regulate fluid flow therethrough. Fifth conduit 18 is connected with sixth conduit 20 between valve 38 and vacuum source 100.

Operation of metering system 10 will now be described. Referring first to FIG. 1, there is shown a reservoir fill operation. Valve 30 is actuated to move to a position wherein reservoir 50 is in fluid communication with decontaminant source 40; valve 32 is actuated to move to a position wherein reservoir 50 is in fluid communication with vacuum source 100; valve 34 is in a default position wherein reservoir 50 is in fluid communication with first end 64 of injector 60; valve 36 is in a default position wherein second end 66 of injector 60 is in fluid communication with a vent to atmospheric pressure; and valve 38 is in a position wherein there is no fluid communication between chamber 80 and vacuum source 100. When vacuum source 100 is activated, a vacuum is created at second end 56 of reservoir 50. As a result, liquid decontaminant flows through conduit 12 from decontaminant source 40 into reservoir 50. Vacuum source 100 remains activated and valve 32 remains in a position wherein reservoir 50 is in fluid communication with vacuum source 100, until the amount of liquid decontaminant inside reservoir 50 reaches a predetermined limit sensed by level sensor 58. In this regard, sensor 58 generates a signal, received by the control unit, indicating that the liquid decontaminant in reservoir 50 has reached a predetermined level. In response to the signal generated by sensor 58, valve 30 is actuated to move to a position terminating fluid communication between reservoir 50 and decontaminant source 40. Vacuum source 100 continues to draw a vacuum at second end 56 of reservoir 50 for a predetermined time period to remove any entrained air inside reservoir 50, second conduit 14, and injector 60. Once the entrained air has been removed, valve 32 is actuated to move to a position terminating fluid communication between reservoir 50 and vacuum source 100, and putting second end 56 of reservoir 50 in fluid communication with a vent to atmospheric pressure.

Before commencing a metered pulse injection operation (described below) chamber 80 is charged with a vacuum. Valve 38 is actuated to move to a position wherein chamber 80 is in fluid communication with vacuum source 100. After chamber 80 has been charged with a vacuum, valve 38 is actuated to move to a position wherein fluid communication between chamber 80 and vacuum source 100 is terminated.

An injector fill operation (see FIG. 2) commences after completion of the reservoir fill operation and charging of chamber 80, as described above. To begin the injector fill operation, valve 36 is actuated to move to a position wherein second end 66 of injector 60 is in fluid communication with vacuum source 100. Valve 34 remains in a default position wherein first end 54 of reservoir 50 is in fluid communication with first end 64 of injector 60, and valve 32 remains in a position wherein second end 56 of reservoir 50 is in fluid communication with a vent to atmospheric pressure.

Figure 2:
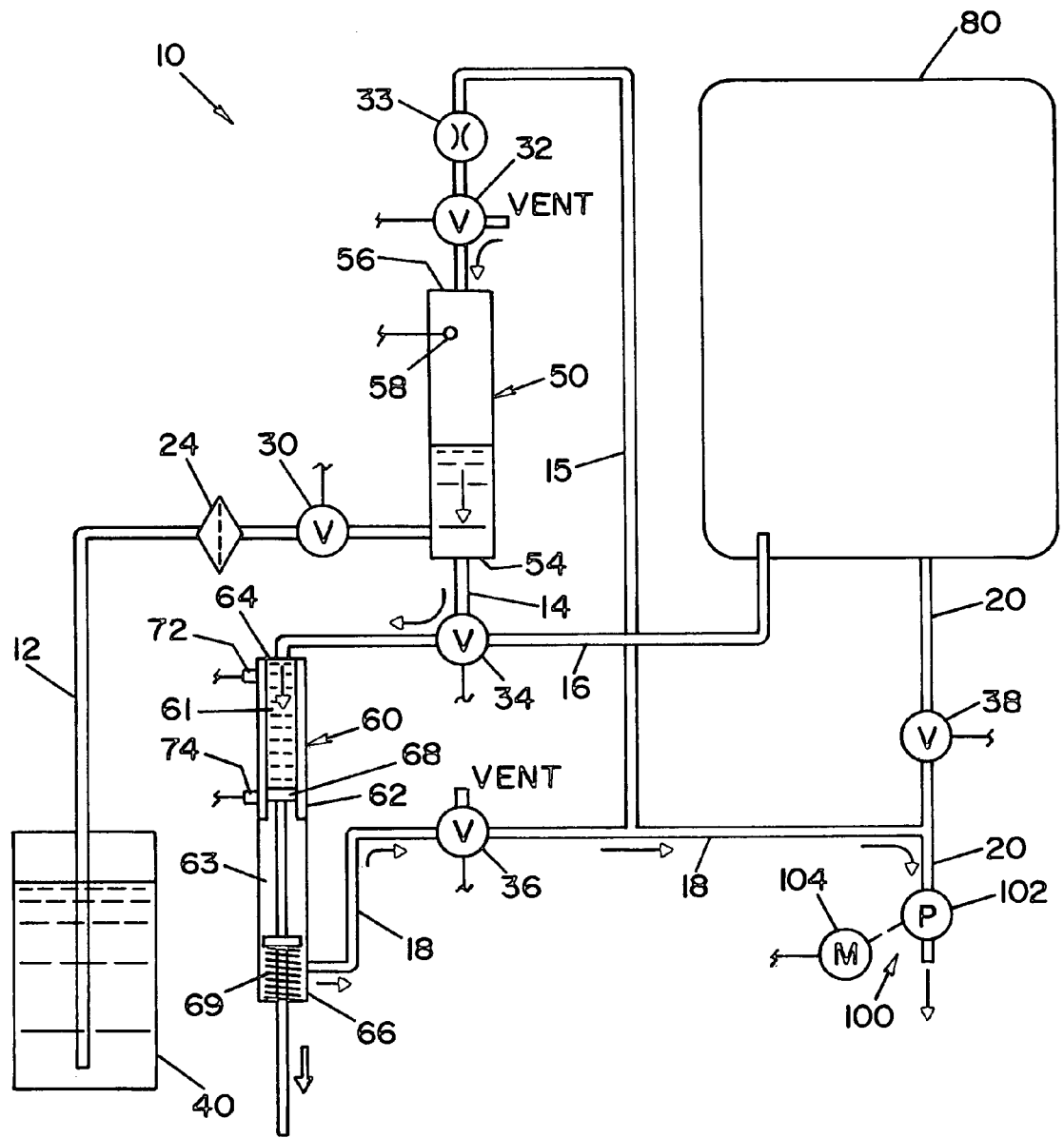
FIG. 2 is a schematic diagram of the system of FIG. 1 illustrating an injector fill operation.

In the illustrated embodiment, piston 68 of injector 60 is initially located at a first position at first end 64 of injector 60 (as verified by activation of switch 72), when the injector fill operation commences. As a vacuum is established at second end 66 of injector 60, piston 68 moves against spring 69 to a second position at second end 66 of injector 60 (as verified by activation of switch 74), as shown in FIG. 2. As piston 68 moves between the first and second positions, liquid decontaminant is drawn from reservoir 50 into head section 61 of cylinder 62. In a preferred embodiment, head section 61 of cylinder 62 is dimensioned to receive a predetermined volume of liquid decontaminant, wherein the predetermined volume is a preferred volume of liquid decontaminant for a single pulse of a decontamination cycle. Valve 36 remains in a position wherein second end 66 of injector 60 is in fluid communication with vacuum source 100.

Figure 3:
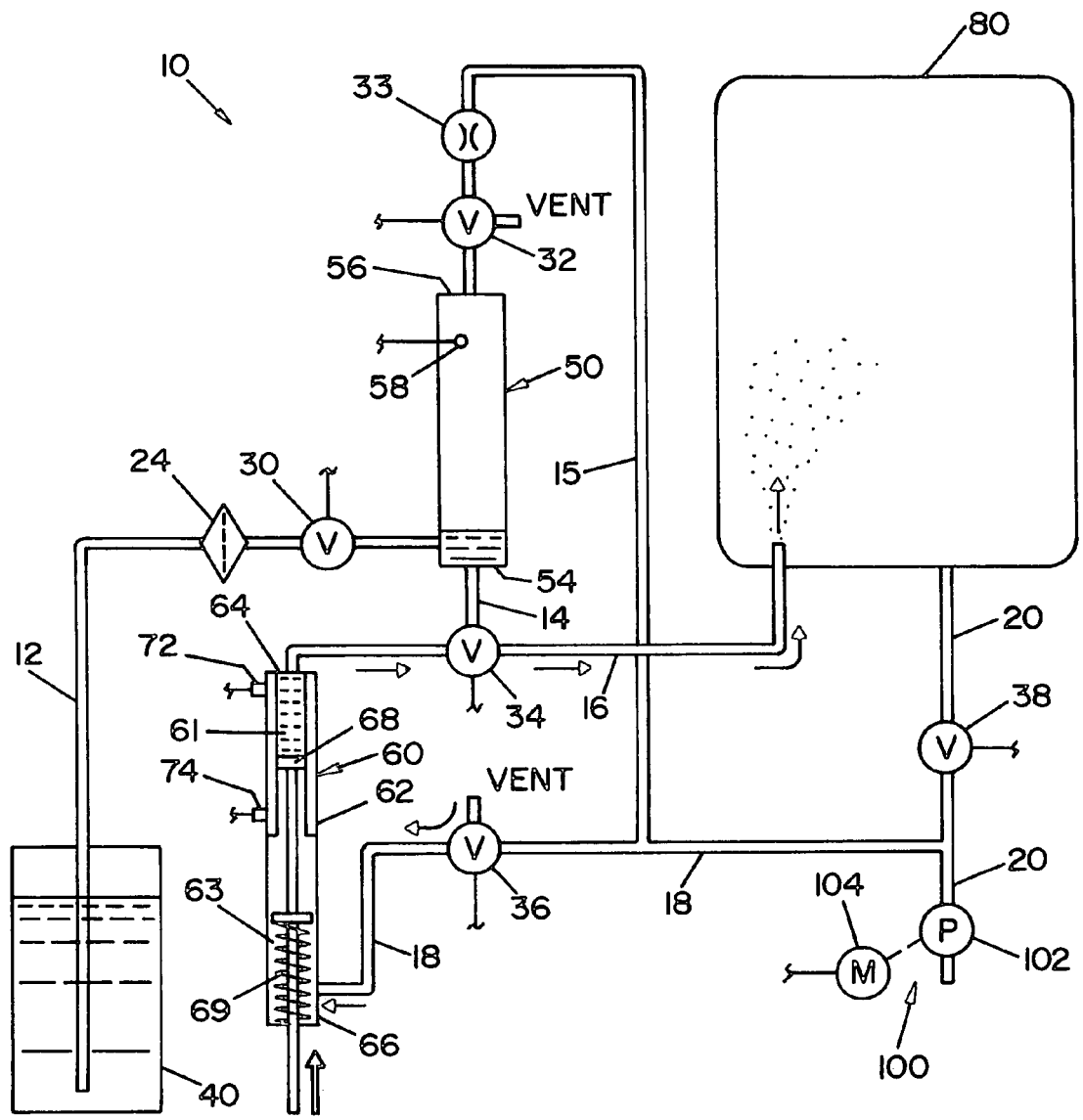
FIG. 3 is a schematic diagram of the system of FIG. 1 illustrating a metered pulse injection operation.

Referring now to FIG. 3, there is shown a metered pulse injection operation. At the appropriate time for injecting a metered pulse of liquid decontaminant into chamber 80, valve 34 is actuated to move to a position wherein first end 64 of injector 60 is in fluid communication with chamber 80; and valve 36 is actuated to move to a position wherein second end 66 of injector 60 is in fluid communication with a vent to atmospheric pressure. Since chamber 80 has been previously charged with a vacuum (as described above), a vacuum is established at first end 64 of injector 60. As a result, spring 69 expands to move piston 68 from the second position at second end 66 of injector 60 (as verified by activation of second switch 74) to the first position at first end 64 of injector 60 (as verified by activation of first switch 72). As a result, liquid decontaminant from head section 61 of cylinder 62 flows from injector 60 into chamber 80. The liquid decontaminant injected into chamber 80 is vaporized therein. After a metered pulse of liquid decontaminant has been injected into chamber 80, valve 34 is actuated to move to the default position, thus terminating fluid communication between first end 64 of injector 60 and chamber 80.

Subsequent metered pulses of liquid decontaminant are injected into chamber 80 by repeating the foregoing injector fill and metered pulse injection operations.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A system for metering a predetermined quantity of a liquid decontaminant into a chamber, the system comprising:

a vacuum source;

a source of the liquid decontaminant;

a reservoir for storing the liquid decontaminant; and an injection means for injecting a predetermined quantity of liquid decontaminant into the chamber, wherein the reservoir is fluidly connectable with the source of the liquid decontaminant, the injection means, and the vacuum source, the injection means is fluidly connectable with the chamber and the vacuum source, and the chamber is fluidly connectable with the vacuum source, and said injection means includes a first member, movable between a first position and a second position, and a second member, wherein liquid decontaminant is introduced into the second member by movement of the first member from the first position to the second position, and liquid decontaminant is introduced into the chamber by movement of the first member from the second position to the first position.

2. A system according to claim 1, wherein said system further comprises:

a first valve for controlling fluid flow between said source of liquid decontaminant and said reservoir;

a second valve for controlling fluid flow between said reservoir and said vacuum source;

a third valve for controlling fluid flow between said reservoir and said injection means and for controlling fluid flow between said injection means and said chamber;

a fourth valve for controlling fluid flow between said injection means and said vacuum source; and a fifth valve for controlling fluid flow between said chamber and said vacuum source.

3. A system according to claim 2, wherein said second valve is movable to a position wherein said reservoir is in fluid communication with atmospheric pressure.

4. A system according to claim 2, wherein said fourth valve is movable to a position wherein said injection means is in fluid communication with atmospheric pressure.

5. A system according to claim 1, wherein said system further comprises:

sensing means for sensing the level of liquid decontaminant in said reservoir, wherein the sensing means generates a signal indicating that the liquid decontaminant in said reservoir has reached a predetermined level.

6. A system according to claim 1, wherein said first member is a piston and said second member is a cylinder.

7. A system according to claim 1, wherein said injection means is dimensioned to receive a predetermined volume of liquid decontaminant from said reservoir.

8. A system according to claim 1, wherein said vacuum source includes a pump.

9. A system according to claim 1, wherein said liquid decontaminant includes hydrogen peroxide.

10. A method for metering a predetermined quantity of a liquid decontaminant into a chamber, the method comprising:

transferring a liquid decontaminant from a source of liquid decontaminant to a reservoir by putting the reservoir in fluid communication with the source of liquid decontaminant and with a vacuum source;

transferring the liquid decontaminant from the reservoir to an injection means by putting the reservoir in fluid communication with the injection means, and putting the injection means in fluid communication with the vacuum source; and metering liquid decontaminant from the injection means to the chamber by puffing injection means in fluid communication with the chamber having a vacuum created therein, wherein the step of transferring liquid decontaminant from the reservoir to the injection means includes moving a first member from a first position to a second position to introduce the liquid decontaminant into the injection means, and wherein the step of metering liquid decontaminant from the injection means to the chamber includes moving the first member from the second position to the first position to introduce the liquid decontaminant into the chamber.

11. A method according to claim 10, wherein a vacuum is created in said chamber by pulling the chamber in fluid communication with said vacuum source.

12. A method according to claim 10, wherein said reservoir is also in fluid communication with atmospheric pressure when transferring the liquid decontaminant from the reservoir to the injection means.

13. A method according to claim 10, wherein said injection means is also in fluid communication with atmospheric pressure when metering liquid decontaminant from the injection means to the chamber.

14. A method according to claim 10, wherein said method further comprises:

sensing the level of the liquid decontaminant in said reservoir as liquid decontaminant is transferred from said source of liquid decontaminant to said reservoir; and generating a signal indicating that the liquid decontaminant in said reservoir has reached a predetermined level.

15. A method according to claim 10, wherein said first member is a piston.

16. A method according to claim 10, wherein said injection means is dimensioned to receive a predetermined volume of liquid decontaminant from said reservoir.

17. A method according to claim 10, wherein said liquid decontaminant includes hydrogen peroxide.

* * * * *